United States Patent [19]

Ohtani et al.

[11] Patent Number: 5,175,341
[45] Date of Patent: Dec. 29, 1992

[54] MONO ESTER OF DICARBOXYLIC ACID AND PROCESS THEREOF

[75] Inventors: Mitsuaki Ohtani, Nara; Takaharu Matsuura, Hyogo, Japan

[73] Assignee: Shionogi & Co., Ltd., Osaka, Japan

[21] Appl. No.: 718,366

[22] Filed: Jun. 20, 1991

Related U.S. Application Data

[62] Division of Ser. No. 448,867, Dec. 12, 1989, Pat. No. 5,047,574.

[30] Foreign Application Priority Data

Dec. 14, 1988 [JP] Japan .................................. 63-315729

[51] Int. Cl.⁵ .............................................. C07C 69/74
[52] U.S. Cl. ...................................................... 560/120
[58] Field of Search ......................................... 560/120

[56] References Cited

U.S. PATENT DOCUMENTS 2,471,790  5/1949  Sowa .................................... 560/120

OTHER PUBLICATIONS

Storme, Bull. Soc. Chim. Belg., 93, pp. 999–1003 (1984).
Klunder, Tetrahedron Letters, 29, pp. 4087–4090 (1985).

Primary Examiner—Michael L. Shippen
Attorney, Agent, or Firm—Wenderoth, Lind & Ponack

[57] ABSTRACT

Optically active mono-esters of dicarboxylic acid of the formula III:

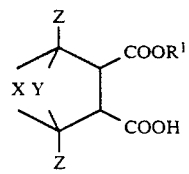

being useful as intermediates for preparing optically active natural products or medicines; asymmetric synthesis process for preparing thereof being characterized by the reaction of an acid anhydride with an (R)- or (S)-arylacetic acid derivative; and the key substances therefor are also claimed.

1 Claim, No Drawings

MONO ESTER OF DICARBOXYLIC ACID AND PROCESS THEREOF

This application is a divisional application of parent application Ser. No. 07/448,867, filed Dec. 12, 1989, now U.S. Pat. No. 5,047,574.

BACKGROUND OF THE INVENTION

1. Field of the Invention

The present invention is useful in the asymmetric syntheses of the various compounds originated from natural products. In more detail, the present invention relates to the mono esters of dicarboxylic acids which are useful in preparing optically active prostaglandins or the like and process for the production thereof.

2. Prior Art

The Diels-Alder reaction (EP-A-0312906), enzymatic hydroylsis of diester moiety or the like is well known as methods for production of optically active half-esters. However, even by such methods, it has been so difficult to prepare a stereochemically pure compound economically on a large scale due to stereochemical impurities, or complicated reactions.

It is significantly useful for the production of various medicinal compounds as well as organic ones from natural sources, if key intermediates are obtained in a high optical purity.

The present invention is designed for syntheses of compounds in much higher optical purity. It is achieved by a stereoselective reaction and by a very easy removal of a small amount of by-products produced in the reaction.

Moreover, the present invention has also an intention of achieving the above-mentioned reaction easily with the inexpensive reagents.

SUMMARY

This invention provides the optically active mono esters of dicarboxylic acid of the formula III:

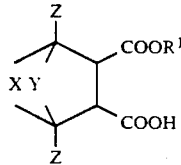

and further provides a process for preparing the compound of the formula III characterized by the reaction of the σ-symmetric dicarboxylic anhydride with arylacetic acid derivative and the removal of arylacetic acid residue. The compounds of the formula III are useful as intermediates for preparing optically active natural products and medicines.

DESCRIPTION OF THE PREFERRED EMBODIMENTS

As a result of the extensive study, the inventors have found that the mono esters of dicarboxylic acids having the desired configuration can be prepared by reacting σ-symmetric acid anhydrides with (R)- or (S)-arylacetic acid derivatives. The present invention is based on this finding.

Though the details are described hereinafter, the by-product which results from this reaction can be removed easily by single crystallization. The asymmetric synthesis the present invention provides is applicable to various σ-symmetric acid anhydrides. The consequent mono esters of dicarboxylic acids are very important as the intermediates for production of such useful compounds obtained from natural sources as prostaglandins, terpenes, aminosugers, nucleotides, alkaloids, and so forth.

The present invention provides these important intermediates, i.e., an optically active mono-ester of a dicarboxylic acid of the formula III:

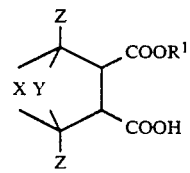

wherein $R^1$ is optionally substituted alkyl, optionally substituted alkenyl, optionally substituted aryl, or optionally substituted aralkyl, —X— is —O—, —S—, —O—O—, —(CH$_2$)m—,

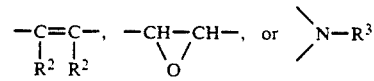

wherein m is an integer of 0 to 4, $R^2$ is hydrogen, methyl, or ethyl, and $R^3$ is hydrogen, methyl, benzyloxycarbonyl, or formyl;

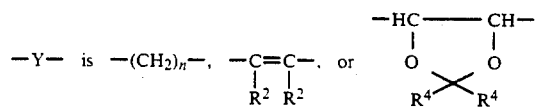

wherein n is an integer of 0 to 3, $R^2$ is the same as defined above, and $R^4$ is hydrogen, methyl, or ethyl; and Z is hydrogen, lower alkyl, or phenyl, excepting those which m and n are identically zero or (1S,2R,3S,4R)-7-oxabicyclo[2.2.1]heptan-2,3-dicarboxylic acid 2-methyl ester.

And also the present invention provides the asymmetric synthesis process for prepareing mono esters of dicarboxylic acid of the formula III:

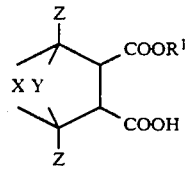

wherein $R^1$, X, Y, and Z each is the same as defined above; being characterized by the reaction of an acid anhydride of the formula I:

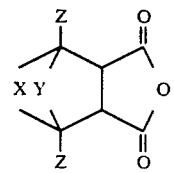

wherein X, Y, and Z each is the same as defined above: with an (R)- or (S)-arylacetic acid derivative of the formula:

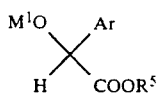

wherein $M^1$ is hydrogen or metal atom, $R^5$ is hydrogen, optionally substituted alkyl, optionally substituted aralkyl, and Ar is optionally substituted aryl; to give an ester of arylacetic acid derivative of the formula II:

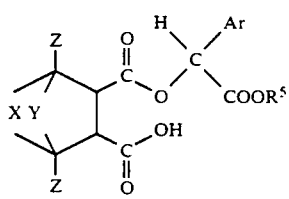       II wherein $R^5$, X, Y, Z, and Ar each is the same as defined above; and subsequent esterification of the said ester II to introduce $R^1$ followed by removal of the arylacetic acid residue or subsequent reaction of the said ester II with a compound IV of the formula:

$R^1OM^2$       IV wherein $R^1$ is optionally substituted alkyl, optionally substituted alkenyl, menthyl, optionally substituted aryl, or optionally substituted aralkyl and $M^2$ is alkali metal or alkaline earth metal.

Moreover, the present invention provides the highly pure key substances, which are produced throughout the reaction process, i.e., the mono esters of (R)- or (S)-arylacetic acid derivative of the formula:

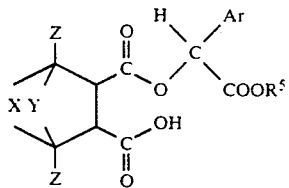       II wherein $R^5$, X, Y, Z, and Ar each is the same as defined above.

The present invention is explained in more detail by referring to the following reaction schemes.

Preparation of mono esters of trans-dicarboxylic acids

Method A

Method Using (R)-Arylacetic Acid Drivatives

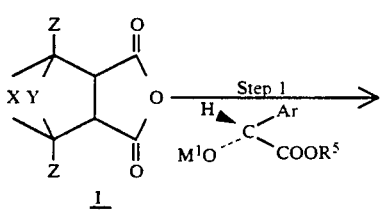

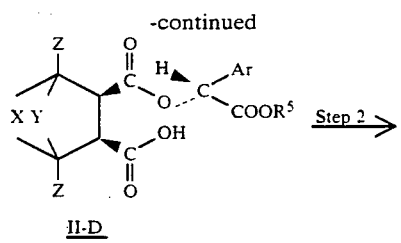

II-D

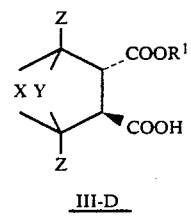

III-D wherein $R^1$, $R^5$, X, Y, Z, Ar, and $M^1$ each is the same as defined before.

Step 1

A prochiral cyclic anhydride having σ symmetry shown by the compound I is allowed to react with a (R)-arylacetic acid derivative in a solvent to give an aimed product II-D.

The reaction is achieved at a temperature of about $-100°$ C. to about $50°$ C., preferably, at about $-78°$ C. to about $0°$ C. within about several ten minutes to several hours.

As a solvent, tetrahydrofuran, diethyl ether, diisopropyl ether, dioxane, 1,2-dimethoxyethane, n-hexane, DMSO, toluene, HMPA, and the like are exemplified.

Depending on the arylacetic acid derivative subjected to the reaction, two types of the aimed products II-D can be obtained. A free carboxylic acid type is represented by II-D(a) and an ester type is represented by II-D(e). Being crystallized easily, the compound II-D(a) can be separated from impurities and subjected to next reaction. The compound II-D(e) is subjected, if necessary, to deprotection in order to convert into the compound II-D(a), which can be subjected to the next reaction.

The deprotection is preferably conducted under neutral to acidic conditions. The ester bond between the arylacetic acid residue and ring-attached carbonyl must be retained during the deprotection. Therefore, alkali conditions are not suitable for this deprotection, since the said ester bond may be cleaved under such conditions. Usually, the deprotection is carried out by catalytic hydrogenoysis using palladium carbon under neutral conditions. In case that the compound II-D has any other functional groups liable to be reduced or double bonds in X or Y, it is hydrogenated at those sites and sometimes gives single bonds consequently. If deprotections without any influence to those sites would be desired, it is recommended that the reaction is carried out under acidic conditions using such reagent as trifluoroacetic acid, aluminum chloride, zinc- acetic acid or the like. The desired protecting group may be removed by thermal decomposition with LiI, LiCl, NaCl, or the like.

Step 2

The aimed compound III-D is prepared by the transesterification with the compound of the formula IV:

$R^1OM^2$  IV wherein $R^1$ and $M^2$ each is the same as defined above. followed by the stereoselective isomerization.

The compound of the formula IV includes an alkoxide, aryloxide, alkenyloxide, menthyloxide, aralkyloxide, or the like with an alkali metal or alkaline earth metal.

The alkali metal or alkaline earth metal alkoxide includes sodium methoxide, lithium methoxide, magnesium ethoxide, or the like.

The alkali metal or alkaline earth metal aryloxide includes sodium phenoxide, lithium phenoxide, magensium phenoxide, sodium α-napthoxide, lithium β-naphthoxide, or the like.

The alkali metal or alkaline earth metal alkenyloxide includes sodium allyloxide, lithium allyloxide, magnesium allyloxide, or the like.

The alkali metal menthyloxide includes sodium menthyloxide, lithium menthyloxide, or the like.

The alkali metal aralkyloxide includes sodium benzyloxide, lithium benzyloxide, or the like.

As a solvent, methanol, ethanol, allylalcohol, phenol, or the like is used, if necessary, menthyl alcohol, pyridine, tetrahydrofuran, or the like may be added.

The reaction is achieved at a temperature of about $-30°$ C. to about 150° C., preferably, at about 0° C. to about 80° C. within about 3 to about 10 hours.

In the Step 1, a small amount of compound represented by the following general formula II'-D:

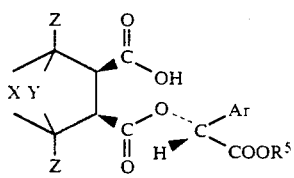

II'-D wherein $R^5$, X, Y, Z, and Ar each is the same as defined above; is obtained as a by-product. If necessary, in order to remove the said by-product quantitatively, it may be converted into a dicarboxylic acid II'-D(a), which remains in mother liquor after recrystallization, by removing the protection group. And the pure aimed product II-D can be applied to the next step 2. The product II-D(e) in the step 1 may be subjected to next reaction without isolation. The ester may be purified by the chromatography.

Method B

Method Using (S)-Arylacetic Acid Derivatives

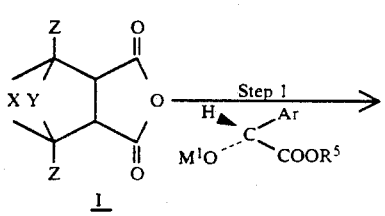

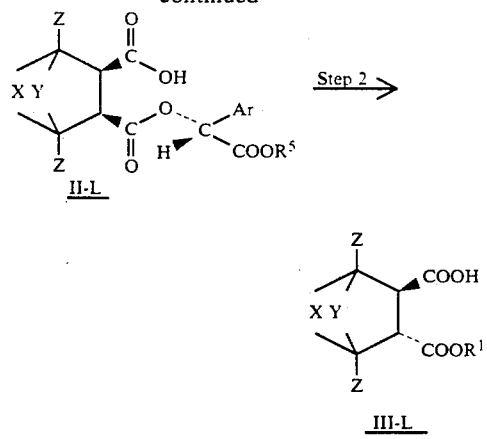

II-L

III-L wherein $R^1$, $R^5$, X, Y, Z, Ar, and $M^1$ each is the same as defined before.

Step 1

According to Step 1 previously mentioned for the (R)-arylacetic acid derivatives, the compound 1 is allowed to react with an (S)-arylacetic acid drivative to give an aimed compound II-L. Depending on the arylacetic acid derivatives subjected to the reaction, two types of the aimed products II-L can be obtained. The free carboxylic acid type and the ester type are represented as II-L(a) and II-L(e), respectively. The compound II-L(a) can be isolated easily by crystallization.

Step 2

According to the fore-mentioned Step 2 for the D isomer, the compound II-L prepared in Step 1 is allowed to react with bases to give an aimed compound III-L.

In the above Step 1, a small amount of the compound II'-L represented by the following general formula II'-L:

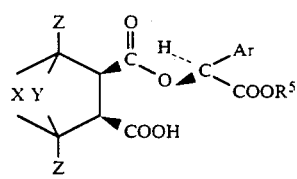

II'-L wherein $R^5$, X, Y, Z and Ar each is the same as defined before is obtained as a by-product. The said by-product can be removed by the same manner as in the case that arylacetic acid derivatives of D-isomer are used. The mixture which contains the compound II'-L(e) can be also be applied to the next reaction without isolation. The ester can be also purified by the chromatography as mentioned above.

If necessary, compound II'-D or II'-L can be transformed into the desired III-L or III-D, respectively by the reaction of Step 2.

Preparation of mono esters of cis-dicarboxylic acids

Preparation of Compound III-D-2

The compounds II (II-D, II'-D, II-L, and II'-L) prepared by the same manner as in Step 1 of Methods A or B for mono esters of trans-dicarboxylic acids are used.

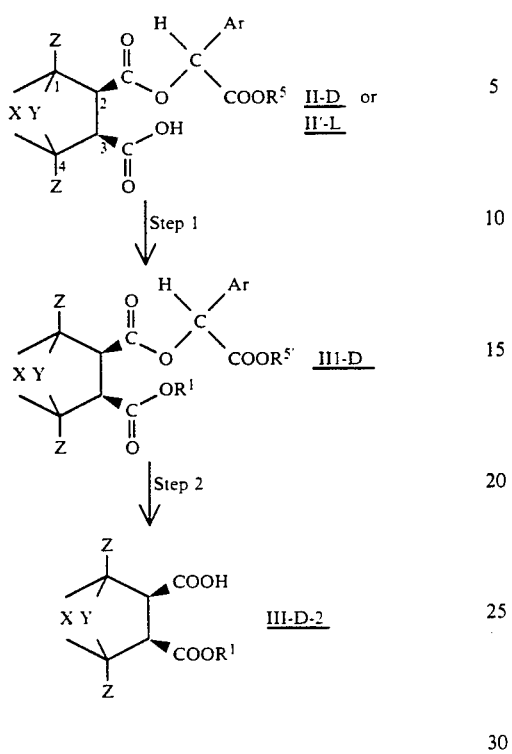

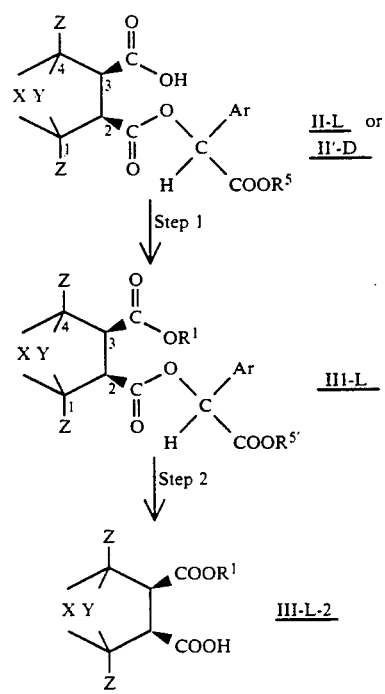

Preparation of Compound III-L-2

In the above reaction scheme, $R^{5'}$ is optionally substituted alkyl, optionally substituted alkenyl, menthyl, optionally substituted aryl, or optionally substituted aralkyl and $R^1$, X, Y, and Z each has the same meaning as defined above.

Step 1

In this step, $R^1$ moiety is introduced by the esterification of the free carboxyl of the compounds II-D or II'-L.

The esterification is carried out retaining the ester linkage between arylacetic acid residue and ring-attached carbonyl and the configuration at 2-position. The reaction is carried out in an usual manner using diazo-compound (e.g., diazomethane, diazoethane, diphenyldiazomethane, phenyldiazomethane), alcohol (e.g., methanol, ethanol, propanol, isopropanol, tert-butanol, benzyl alcohol, menthol, phenol, substituted phenol (nitrophenol, methylphenol, chlorophenol, methoxyphenol), naphthol, or the like which have a desired $R^1$ formative group. In order to facilitate the reaction, an acid such as p-toluenesulfonic acid, formic acid, sulfuric acid, hydrochloric acid, or the like may be added.

Step 2

In this step, the cis type compound of the present invention III-D-2 is prepared by the cleavage of the ester linkage between arylacetic acid residue and ring-attached carbonyl.

As the configuration must be retained during the reaction, the reaction is usually carried out reductively using palladiumcarbon under neutral conditions.

In the above reaction scheme, $R^1$, $R^{5'}$, X, Y, and Z each has the same meaning as defined above.

The compound III-L-2 is prepared from the compound II-L or II'-D in the same manner as in the above Steps 1 and 2 for III-D-2.

The arylacetic acid esters, the compounds of the present invention of the formula II, have four types of stereoisomers II-D, II'-D, II-L, and II'-L.

The mono esters of dicarboxylic acid, the compounds of the present invention of the formula III, have four asymmetric carbon atoms, therefore, they have eight types of stereoisomers. This invention includes all of them, that is, the compounds having the configuration shown by the following formulas;

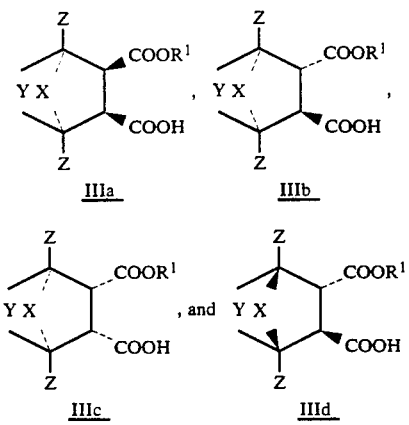

wherein, $R^1$ X, Y, and Z each has the same meaning as defined above, and their enantiomers.

The following explanations are given for the terms used in the above definition.

The term "alkyl" includes methyl, ethyl, isopropyl, n-propyl, n-butyl, isobutyl, t-butyl, sec-butyl, pentyl, neopentyl, and the like.

The term "alkenyl" includes 2-propenyl, 2-butenyl, 3-butenyl, 2-methyl-2-propenyl, 3-methyl-3-butenyl, 2-pentenyl, 3-pentenyl, 4-pentenyl, prenyl, and the like.

The term "aryl" includes phenyl, α- or β-naphthyl, and the like.

The term "aralkyl" includes benzyl, phenethyl, naphthylmethyl, and the like.

The term "metal atom" chiefly refers to alkali metal atom which includes lithium, sodium, potassium, and the like and alkalin earth metal atom which includes magensium, calcium, and the like and also refers to zinc and the like.

The term "bicycle" includes norborane type (e.g., bicyclo[2.2.1]heptane, bicyclo[2.2.1]hept-5-en, or the like), 7-oxabicyclo[2.2.1]heptane, 7-oxabicyclo[2.2.1]hept-5-ene, 7-azabicyclo[2.2.1]heptane, 7-azabicyclo[2.2.1]hept-5-ene, 7-thiabicyclo[2.2.1]heptane, 7-thiabicyclo[2.2.1]hept-5-ene, and the like.

As the acid anhydride, a bi- or tricyclic anhydride having σ-symmetry can be applied.

The substituent, which may exist on previous mentioned alkyl, alkenyl, aryl, and aralkyl includes above-mentioned alkyl and alkoxy, halogen, amino, amino derivative, nitro, and the like.

The term "alkoxy" includes methoxy, ethoxy, propoxy, isopropoxy, butoxy, pentyloxy, and the like.

The term "halogen" includes fluorine, chlorine, bromine, and iodine.

The term "amino derivative" includes hydroxyamino, alkylamino, and the like.

The following examples and referential examples are included to explain the embodiment of the present invention in more detail, but these are not intended to limit the scope of the invention.

The abbreviations used throughout the tables, examples referential examples have the meaning as shown below.

| Me: | methyl. | CH$_2$Ph: | benzyl. |
|---|---|---|---|
| Et: | ethyl. | CHPh$_2$: | benzhydryl. |
| Bu: | butyl. | Ph: | phenyl. |
| THF: | tetrahydrofuran, | | |
| DMF: | dimethylformamide, | | |
| HMPA: | hexamethylphosphoramide, | | |
| D-Mande: | D-mandelic acid and its ester, | | |
| L-Mande: | L-mandelic acid and its ester, | | |
| PCC: | pyridinium chlorochromate, and | | |
| PMB: | p-methoxybenzyl. | | |

EXAMPLE 1

Preparation of (1S,2R,3S,4R)-bicyclo[2.2.1]hept-5-en-2, 3-dicarboxylic acid, 2-(benzyl D-mandelate) ester II-1-D(e1)

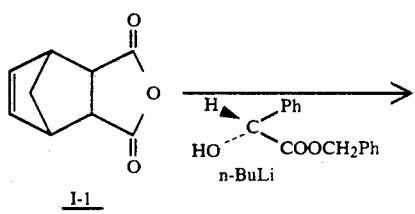

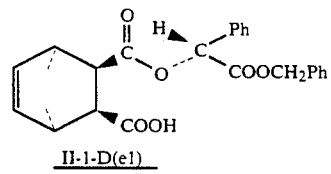

In a nitrogen atmosphere, a solution of benzyl D-mandelate (5.33 g, 22.0 mmol) in 50 ml of THF was cooled to −78° C., then 13.13 ml (21.0 mmol) of 1.6M solution of n-butyllithium in hexane was added dropwise and the mixture was stirred for 15 minutes. To the reaction mixture was added a solution of 3.32 g (20.0 mmol) of bicyclo[2.2.1]hept-5-en-2-endo, 3-endo-dicarboxylic anhydride I-1 in 20 ml of THF and the resulting mixture was stirred for an hour at −78° C. The reaction mixture was acidified with 2N hydrochloric acid and the product was extracted with ethyl acetate. The organic layer was washed with water and an aqueous solution of sodium chloride and concentrated to give 9.33 g of the mixture of the aimed product II-1-D(e1) and its by-product II'-1-D(e1). The aimed product II-1-D(e1) was purified by column chromatography on silica gel (toluene-ethyl acetate).

IR(film)νmax: 3600-2400, 1748, 1710, 1498, 1456, 1342, 1257, 1208, 1165, 1084, 1072, 912, 732, 696 cm$^{-1}$.

$^1$HNMR(CDCl$_3$TMS)δ ppm: 1.33(ABq, Apart, J=8.9 Hz; 1H), 1.48(ABq, Bpart, J=8.9 Hz, 1H), 3.16(br. s, 1H), 3.21(br. s, 1H), 3.30(dABq, Apart, J=3.2, 10.2 Hz, 1H), 3.47(dABq, Bpart, J=3.4 Hz, 10.2 Hz, 1H), 5.13(s, 2H), 5.97(s, 1H), 6.11(dABq, Apart, J=2.9 Hz, 5.9 Hz, 1H), 6.28(dABq, Bpart, J=2.8, 5.9 Hz, 1H), 7.13∼7.52(m, 10H).

EXAMPLE 2-7

According to the procedure in Example 1, the reaction was conducted as shown by following reaction formula to give the aimed compounds II-D(e), II-D(a), and II-L(e). The reaction conditions are shown in Table 1.

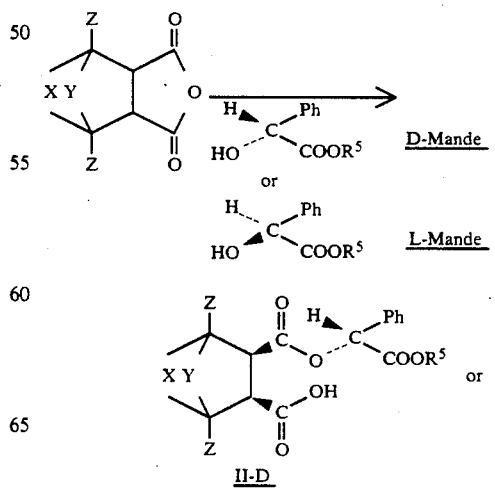

-continued

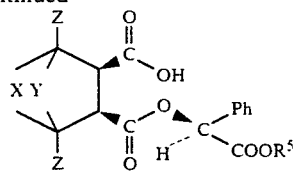

II-L wherein $R^5$, X, Y, and Z each has the same meaning as defined before.

$^1$HNMR(CDCl$_3$-TMS)δ ppm: 1.37~2.00(m, 6H), 2.62(br. s, 2H), 3.06(dABq, Apart, J=3.0, 12.0 Hz, 1H), 3.22(dABq, Bpart, J=3.0, 12.0 Hz, 1H), 3.74(s, 3H), 6.01(s, 1H), 7.33~7.55 (m, 5H).

$[α]_D = -70.2° \pm 0.6°$ (CHCl$_3$, C=1.965%, 24° C.)

The other products were treated with the same procedure to isolate the compounds II-1-D(e1), II-1-D(e2), II-1-D(e3), II-2-D(a1), and II-2-L(e1), respectively.

TABLE 1

$$\begin{array}{c} Z \\ X\diagdown Y \diagup O \\ Z \diagup \| \\ O \end{array} \xrightarrow[\text{or}]{\text{D-Mande}} \text{II-D(e), II-D(a) or II-L(e)}$$
L-Mande

I

| Ex. No. | I (Z, X, Y) | Mandelic acid and its ester g (mmol) | D or L | $R^5$ | g (mmol) | n-BuLi ml (mmol) | ZnCl$_2$ g (mmol) | II-D(e), II-D(a) or II-L(e) Crude: g (Yield: %) | Compound No. |
|---|---|---|---|---|---|---|---|---|---|
| 2 | (norbornyl) | 1.83 (11.2) | D | CH$_2$Ph | 2.97 (12.3) | 7.30 (11.7) | 0.796 (5.84) | II-D(e) / 5.75 | II-1-D(e1) |
| 3 | (norbornyl) | 14.68 (89.4) | D | CHPh$_2$ | 28.47 (89.4) | 55.9 (89.4) | — | II-D(e) / 43 | II-1-D(e2) |
| 4 | (norbornyl) | 1.64 (9.99) | D | Me | 1.82 (11.0) | 6.40 (10.2) | — | II-D(e) / 2.86 (87) (II-1-D(e3): II'-1-D(e3) = 78:22) | II-1-D(e3) |
| 5 | (norbornyl) | 47.6 (286) | D | Me | 47.6 (287) | 179 (286) | — | II-D(e) / 91 (96) (II-2-D(e1): II'-2-D(e1) = 82:18) | II-2-D(e1) |
| 6 | (norbornyl) | 1.66 (10.0) | D | H | 1.52 (10.0) | 12.5 (20.0) | — | II-D(e) / 2.57 (81) (II-2-D(a1): II'-2-D(a1) = 50:50) | II-2-D(a1) |
| 7 | (norbornyl) | 14.39 (86.6) | L | CHPh$_2$ | 30.35 (95.3) | 64.0 (96.0) | — | II-L(e)] / 56.77 | II-2-L(e1) |

In Table 1, the mixture of the aimed compound II-2-D(e1) and its by-product II'-2-D(e1), which was prepared in Example 5, was chromatographed on silica gel with toluene-ethyl acetate to isolate 75 g of the aimed compound II-2-D(e1) in 78.6% isolated yield.

Anal. Calcd. (%) for C$_{18}$H$_{20}$O$_6$ 0.2H$_2$O: C, 64.35; H, 6.13; Found (%): C, 64.37; H, 6.49.

EXAMPLE 8

Preparation of (1R,2R,3S,4S)-bicyclo[2.2.1]heptan-2,3-dicarboxylic acid, 2-(D-mandelic acid) ester II-2-D(a1)

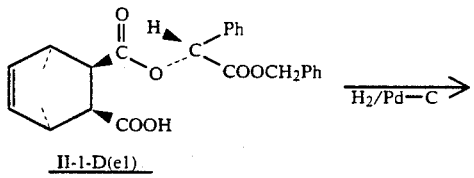

II-1-D(e1)

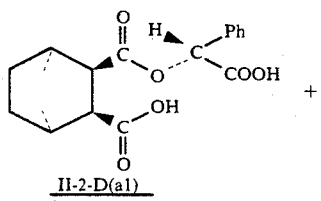

II-2-D(a1)

+

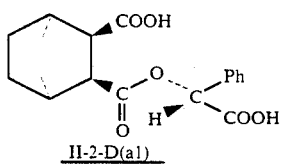

II'-2-D(a1)

To a solution of 4.06 g (10.0 mmol) of crude product II-1-D(e1) in 30 ml of methanol was added 0.4 g of 10% palladiumcarbon and the mixture was stirred in a hydrogen atmosphere under ordinary pressure at room temperature for 1.5 hours. The reaction mixture was filtered to remove the catalyst and the filtrate was concentrated. The residue was partitioned between ethyl acetate and 5% aqueous solution of sodium hydrogencarbonate and the aqueous layer was separated. The organic layer was extracted with water. The aqueous layers were collected and washed with ethyl acetate. After acidification with 2N hydrochloric acid the mixture was extracted with ethyl acetate. The organic layer was washed with an aqueous solution of sodium chloride and concentrated to give 3.14 g of the crude product II-2-D(a1) in 99% yield from acid anhydride. Compound II-2-D(a1): Compound II'-2-D(a1)=86:14 (Determined by HPLC).

The desired compound II-2-D(a1) was isolated by recrystallization from ethyl acetate. (2.05 g, yield 64%).

A mother liquour was concentrated and the residue was recrystallized from dichloromethane to give by-product II'-2-D(a1).

Compound II-2-D(a1)

Mp. 164°-166° C.

Anal. Calcd. (%) for $C_{17}H_{18}O_6$: C, 64.13; H, 5.71; Found (%): C, 63.83; H, 5.73.

$^1$HNMR(CDCl$_3$, TMS)δ ppm: 1.46(br. s, 4H), 1.57~1.75(m, 1H), 1.84~2.08(m, 1H), 2.40~2.62(m, 2H), 3.02(dABq, Apart, J=3.6, 11.6 Hz, 1H), 3.29(dABq, Bpart, J=4.4, 11.6 Hz, 1H), 5.86(s, 1H), 7.33~7.65(m, 5H).

$[α]_D = -117.1°±0.8°$ (MeOH, c=1.934, 25° C.).

Compound II-2-D(a1)

Mp. 157°-158° C.

Anal. Calcd. (%) $C_{17}H_{18}O_6$: C, 64.13; H, 5.71; Found (%): C, 64.02; H,5.57.

$^1$H-NMR(CDCl$_3$-TMS)δ ppm: 1.30~1.66(m, 4H), 1.69~1.87(m, 1H), 1.96~2.13(m, 1H), 2.60(br.s, 2H), 3.04(dABq, Apart, J=2.8, 12.1 Hz, 1H), 3.13(dABq, Bpart, J=3.8, 12.1 Hz, 1H), 5.84(s, 1H), 7.33~7.58(m, 5H).

$[α]_D = -81.8°±0.6°$ (MeOH, C=2,005%, 25° C.)

EXAMPLE 9

The compound II-1-D(e1) prepared in Example 2 was allowed to react by the same procedure as described in Example 8 to give the following dicarboxylic acid II-2-D(a1).

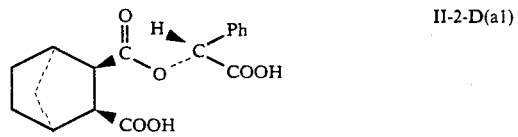

II-2-D(a1)

EXAMPLE 10

The compounds II-1-D(e3) and II-2-D(e1) which were prepared in Example 4 and 5, respectively, were allowed to react with LiI in DMSO to give above-mentioned dicarboxylic acid II-2-D(a1).

EXAMPLE 11

The compound II-2-L(e1) prepared in Example 7 was allowed to react by the same procedure as described in Example 8 to give the following dicarboxylic acid II-2-L(a1).

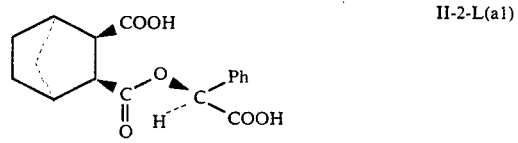

II-2-L(a1)

Mp. 162°-164° C.

$[α]_D = +113.2°±1.5°$ (MeOH, C=1.0075%, 23.5° C.).

EXAMPLE 12

Preparation of (1S, 2R, 3S, 4R)-bicyclo [2.2.1]hept-5-en-2,3-dicarboxylic acid, 2-(D-mandelic acid) ester II-1-D(a1)

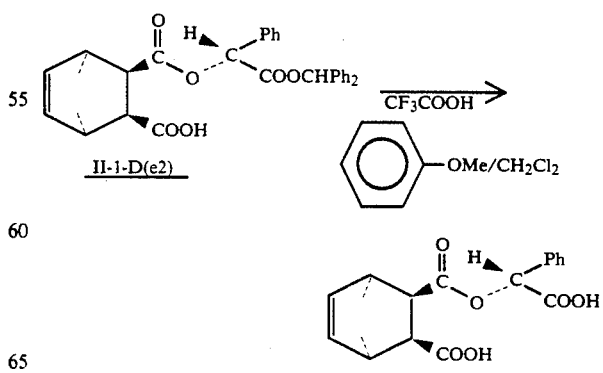

II-1-D(e2)

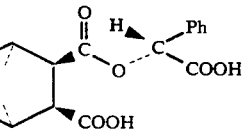

II-1-D(a1)

To a cooled solution to 0° C. of 43 g of the crude product II-1-D(e2) in 60 ml of dichloromethane were added 18 ml of anisole and 50 ml of trifluoroacetic acid and the mixture was stirred for 1 hour. The reaction mixture was concentrated and the residue was partitioned between ethyl acetate and 5% aquous solution of sodium hydrogen carbonate. The aqueous layer was separated, washed with ethyl acetate, acidified with 2N hydrochloric acid, and extracted with ethyl acetate. The organic layer was washed with a saturated aqueous solution of sodium chloride, concentrated, and dried to give a crude II-1-D(a1) [II-1-D(a1): II'-1-D(a1)=74:26 (Determined by HPLC). The crude product was recrystallized from ethyl acetate to give 13.37 g of aimed compound II-1-D(1) in 47% yield.

Mp. 169°-171° C.

Anal. Calcd. (%) for $C_{17}H_{16}O_6$: C, 64.55; H, 5.10; Found (%): C, 64.46; H, 5.12.

IR(CHCl$_3$): 3500-2400, 1734, 1438, 1375, 1342, 1256, 1168, 1146, 1072 cm$^{-1}$.

$^1$H-NMR(CDCl$_3$-TMS)δ ppm: 1.36(ABq, Apart, J=7.2 Hz; 1H), 1.51 (ABq, Bpart, J=7.2 Hz, 1H), 3.15(br. s, 2H), 3.43(dABq, Apart, J=2.9, 10.4 Hz, 1H), 3.53(dABq, Bpart, J=3.1, 10.4 Hz, 1H), 5.86(s, 2H), 6.14~6.33(m, 2H), 7.32~7.62(m, 5H).

[α]$_D$= −159.5±1.0° (MeOH, C=1.993%, 24° C.).

EXAMPLE 13

According to the procedure in Examples 1 and 8, the reaction using the compound I-2 was conducted to give the aimed compound II-2-D(a1)

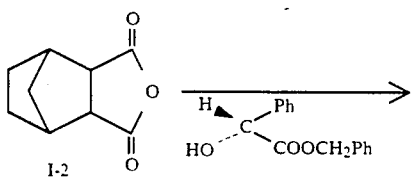

I-2

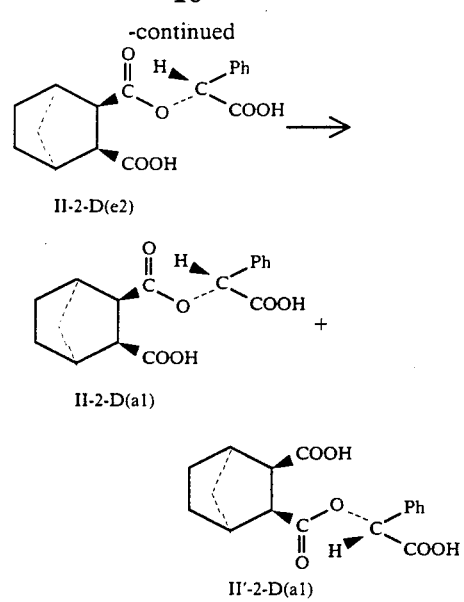

II-2-D(e2)

II-2-D(a1)

II'-2-D(a1)

Bicyclo[2.2.1]heptan-2-endo,3-endo-dicarboxylic anhydride I-2 (1.66 g, 10.0 mmol) was allowed to react with 2.66 g (11.0 mmol) of benzyl D-mandelate in the presence of 6.40 ml (10.2 mmol) of n-BuLi. Without purification, the intermediate II-2-D(e2) was subjected to hydrogenolysis to give 2.64 g of the crude aimed product II-2-D(a1) : in yield 83% (II-2-D(a1): II'-2-D(a1)=80: 20), which was recrystallized from ethyl acetate to isolate 1.47 g of the aimed II-2-D(a1) in 46% yield.

The intermediate II-2-D(e2) can be purified by column chromatography on silica gel.

$^1$H-NMR(CDCl$_3$-TMS)δ ppm: 1.32~1.97(m, 6H),2.55(br. s, 1H), 2.60(br. s, 1H), 2.98(dABq,Apart, J=3.7, 11.6 Hz, 1H), 3.18(dABq, Bpart, J=3.9, 11.6 Hz, 1H), 5.14(s, 2H), 6.03(s, 1H), 7.15~7.52 (m, 10H)

EXAMPLES 14 to 16

The reaction was conducted according to the procedure in Example 13 to give the aimed product II-2-D(a1). The reaction conditions are shown in Table 2.

TABLE 2

$$I \xrightarrow{\text{D-Mande}} X \rightleftharpoons II\text{-D}(e) + X \longrightarrow II\text{-2-D}$$

Structures shown: I, II-D(e), II-D(a), II'-D(e)

| Ex. No. | I g (mmol) | R² | D-Mandelate g (mmol) | n-BuLi ml (mmol) | MgBr₂ | II-D(e) | II-D(a) Crude Yield: g [Crude Yield (%)] | Comd. No. |
|---|---|---|---|---|---|---|---|---|
| 14 | 1.64 (10.0) | CH₂Ph | 2.67 (11.0) | 6.60 (10.6) | Mg: 0.125 (g) 5.15 (mmol) | II-1-D(c1) | 2.24 (70) (II-2-D(a1): II'-2-D(a1) = 50:50) | II-2-D(a1) |
| 15 | 1.42 (8.68) | CH₂—C₆H₄—OMe | 2.59 (9.51) | 5.60 (8.96) | — | II-1-D(c4) | 2.04 (74) (II-2-D(a1): II'-2-D(a1) = 82:18) | II-2-D(a1) |
| 16 | 1.66 (10.0) | CHPh₂ | 3.50 (11.0) | 6.25 (10.0) | — | II-2-D(c3) | 3.05* (96) (II-2-D(a1): II'-2-D(a1) = 73:27) | II-2-D(a1) |

*Recrystallization from ethyl acetate gives 1.74 g of the aimed product in 55% isolated yield. The aimed product in Examples 14 and 15 also isolated in the same method.

EXAMPLE 17

Preparation of (1R,2S,3S,4S)-2-methoxycarbonyl-3-carboxybicyclo[2.2.1]heptane III-2-D-1

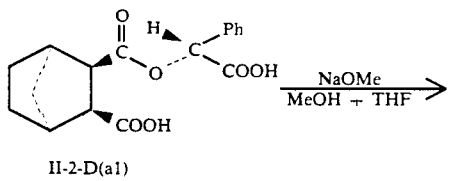

II-2-D(a1)

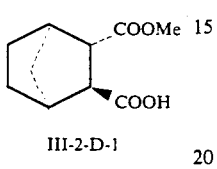

III-2-D-1

In a nitrogen atmosphere, a mixture of 5.51 g (17.3 mmol) of compound II-2-D(a1), 40 ml of THF, 50 ml of methanol, and 22.0 ml (44.0 mmol) of sodium methoxide (2M solution in methanol) was refluxed for 4 hours. To the reaction mixture was added 2N hydrochloric acid and the mixture was extracted with ethyl acetate. The organic layer was washed with water and a saturated aqueous solution of sodium chloride, and concentrated. The residue was dissolved in dichloromethane and washed three times with water. The organic layer was concentrated to give 3.22 g of the desired compound III-2-D-1 in 94% yield.

Mp. 59°–60° C.

Anal. Calcd. (%) for $C_{10}H_{14}O_4$: C, 60.58; H, 7.13; Found (%): C, 60.66; H, 7.08.

$^1$H-NMR(CDCl$_3$-TMS)δ ppm: 1.20~1.74(m, 6H), 2.59(br. s, 1H), 2.69(br. s, 1H), 2.79(d, J=5.4 Hz, 1H), 3.27(dd, J=3.8, 5.4 Hz, 1H), 3.69(s, 3H).

$[α]_D$= +38.4°±0.4° (MeOH, c=2.002, 25° C.).

EXAMPLE 18

Preparation of (1S, 2R, 3R, 4R)-2-methoxycarbonyl-3-carboxybicyclo[2.2.1]heptane III-2-L-1

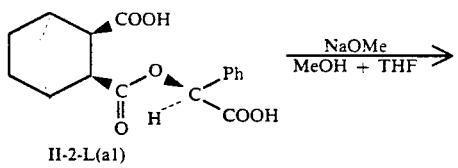

II-2-L(a1)

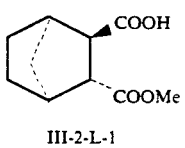

III-2-L-1

According to the procedure in Example 17, the reaction using the compound II-2-L(a1) as a starting material was conducted Compound II-2-L(a1) was an enantiomer of the starting material in Example 17. The reaction was carried out under following conditions:

15.27 g (48.0 mmol) of the compound II-2-L(a1),
55 ml of methanol,
60 ml of THF, and
60 ml (120 mmol) of sodium methoxide (2M in methanol);

to give 7.46 f of the aimed compound III-2-L-1 in 78% yield.

Mp. 59°–60° C. $[α]_D$= −38.3°±0.4° (MeOH, C=2.013%, 25° C.).

EXAMPLE 19

Preparation of (1S,2S,3S,4R)-3-carboxy-2-methoxycarbonylbicyclo[2.2.1]hept-5-ene III-1-D-1

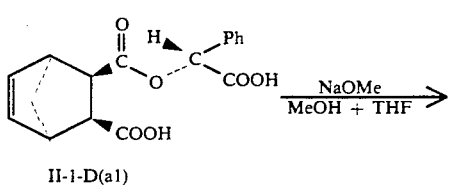

II-1-D(a1)

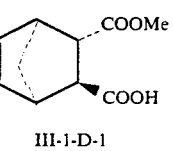

III-1-D-1

According to the procedure in Example 17, 15 g (47.4 ml) of the compound II-1-D(al) was allowed to react with 71.1 ml (142 mmol) of sodium methoxide (2M in methanol) in 50 ml of methanol and 100 ml of THF to give 7.96 g of the aimed compound III-1-D-1 in 93.2% yield.

Mp. 78°–79° C.

Anal. Calcd. (%) for $C_{10}H_{12}O_4$: C, 61.21; H, 6.17; Found (%): C,60.89; H,6.13.

IR(CHCl$_3$): 3400–2400, 1729, 1708, 1438, 1422, 1335, 1311, 1271, 1245, 1190, 1175, 1162, 1114, 1022 cm$^{-1}$.

$^1$H-NMR(CDCl$_3$-TMS)δ ppm: 1.48(ABq, Apart, J=8.0 Hz, 1H), 1.63(ABq, Bpart, J=8.0 Hz, 1H),2.66(dd, J=1.6, 4.6 Hz, 1H), 3.14(br. s, 1H),3.30(br. s, 1H), 3.43(dd, J=3.6, 4.6 Hz, 1H) 3.73(s, 3H), 6.14(dABq, Apart, J=2.9, 5.5 Hz, 1H), 6.29(dABq, Bpart, J=3.1, 5.5 Hz, 1H).

$[α]_D$= +138.1°±0.9° (MeOH, C=2.005%, 24° C.).

EXAMPLE 20

Preparation of (1R,2R,3S,4S)-bicyclo[2.2.1]heptan-2,3-dicarboxylic acid, 2-(D-mandelic acid) ester II-2-D(a1)

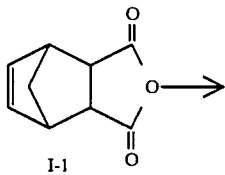

I-1

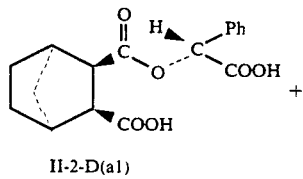

II-2-D(a1)

-continued

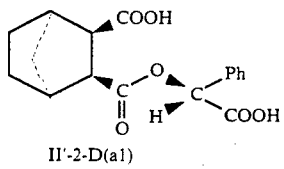

II'-2-D(a1)

In a nitrogen atmosphere, 0.447 g (11.1 mmol) of 60% sodium hydride was washed with hexane, dried under reduced pressure, and suspended in 10 ml of THF. To the suspension was added a solution of 2.69 g (11.1 mmol) of benzyl D-mandelate in 30 ml of THF and the mixture was stirred for 30 minutes. The reaction mixture was cooled to −78° C. and a solution of 1.64 g (10.0 mmol) of bicyclo[2.2.1]hept-5-en-2-endo, 3-endo-dicarboxylic anhydride I-1 in 10 ml of THF was added dropwise. After addition, the resulting mixture was warmed to 0° C. under stirring. The usual workup gives the half-ester, which was subjected to deprotection according to the procedure in Example 8 to give 2.04 g of the crude product in 64% yield. (Compound II-2-D(al):Compound II'-2-D(a1)=59: 41).

EXAMPLE 21

Preparation of (1R,2R,3R,4S)-bicyclo[2.2.1]hept-5-en-2,3-dicarboxylic acid, 2-methyl ester III-1-L-1

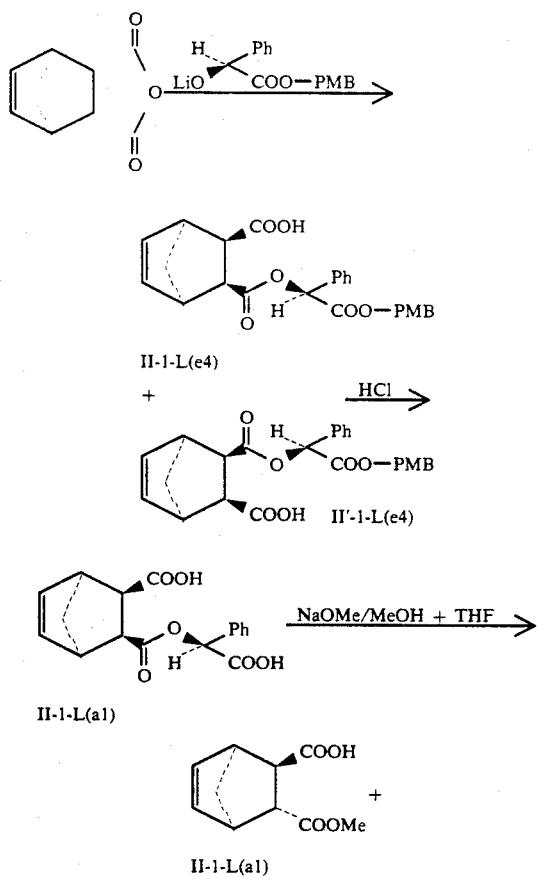

-continued

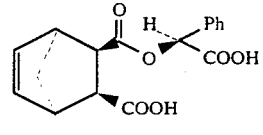

II'-1-L(a1)

According to the procedure in Example 1, the reaction using p-methoxybenzyl L-mandelate in place of benzyl D-mandelate was conducted to give a crud product mainly containing the compound II-1-L(e4), which was subjected to further reaction without isolation.

To a solution of 30.6 g (70 mmol) of the above crude product in 160 ml of acetonitrile was added 35.9 ml (70 mmol×6) of conc. hydrochloric acid and the mixture was stirred for 16 hours at room temperature. The reaction mixture was adjusted to pH 4 with 4N NaOH, then made alkaline with an aqueous sodium hydrogencarbonate under ice-cooling, and then washed with ethyl acetate. The organic layer was further extracted with water and the combined aqueous layer was acidified with conc. hydrochloric acid to pH 2 and extracted with ethyl acetate. The organic layer was washed with water, dried over anhydrous sodium sulfate, concentrated under reduced pressure to give a crystalline residue. The crude product (mixture of II-1-L(a1) and II'-1-L(a1) in the ratio of 85:15 (by HPLC)) was recrystallized with ethyl acetate to give 11.2 g of the compound II-1-L(a1) in 50.2% yield.

mp. 168° to 170° C.

The IR and $^1$H-NMR data of the compound II-1-L(a1) were identical with those of compound II-1-D(a1), respectively.

$[\alpha]_D$= +160.5°±1.0° (MeOH, 23.5° C., c=2.002%)

According to the procedure in Example 17, 345 mg of the compound III-1-L-1 was prepared from 601 mg of the compound II-1-L(a1) in 92.7% yield.

$[\alpha]_D$= −140.8°±0.9° (MeOH, 23° C., c=2.018%)

mp. 78°–79° C.

EXAMPLE 22

Preparation of (1R,2S,3R,4S)-7-oxabicyclo[2.2.1]heptan-2,3-dicarboxylic acid, 2-D-mandelic acid ester II-3-D(a1)

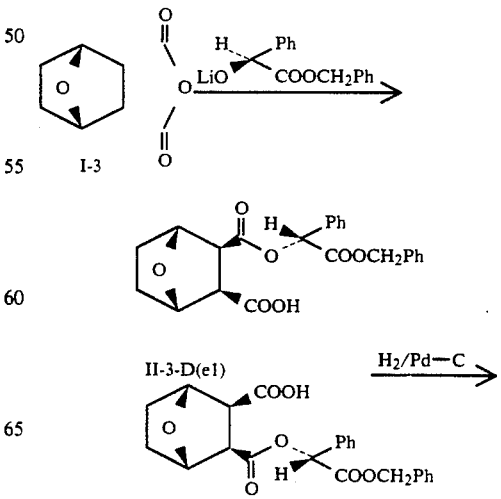

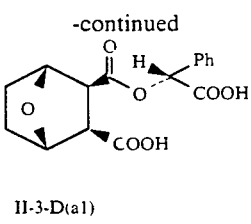

II-3-D(a1)

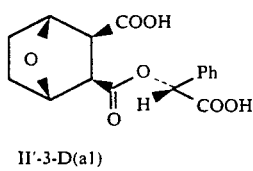

II'-3-D(a1)

According to the procedure in Examples 1 and 8, the mixture of the compounds II-3-D(a1) and II'-3-D(a1) was prepared from 10.5 g (62 mmol) of the compound I-3. (II-3-D(a1) : II'-3-D(a1)=73: 27 (by HPLC)). From the mixture, 7.1 g of the compound II-3-D(a1) and 1.5 g of the compound II'-3-D(a1) was isolated by recrystallization in 35.8% and 7.6% yield, respectively.

Compound II-3-D(a1)

mp. 175°–177° C.

Anal. Calcd. (%) for $C_{16}H_{16}O_7$: C, 59.99; H, 5.04; Found (%): C, 59.85; H, 5.04.

$^1$HNMR($CD_3OD$-TMS)δppm: 1.55~1.88(m,4H), 3.13(ABq, A-part, J=9.6 Hz, 1H), 3.19(ABq, B-part, J=9.6 Hz, 1H), 4.83~4.90(m, 2H), 5.85(s,1H), 7.35~7.65(m,5H). IR(Nujol)νmax: 3480~2200, 1733, 1712, 1659, 1229, 1220, 1185, 1011, 969, 936, 766, 735, 696 cm$^{-1}$.

$[α]_D$ −111.9°±1.5° (MeOH, 23° C., C=1.013%)

Compound II'-3-D(a1)

mp. 133°–135° C.

Anal. Calcd. (%) for $C_{16}H_{16}O_7$·$0.5H_2O$: C, 58.35; H, 5.21; Found (%): C, 58.33; H, 5.48.

$^1$HNMR($CD_3OD$-TMS)δppm: 1.55~1.90(m,4H), 3.12(ABq, A-part, J=9.6 Hz, 1H), 3.22(ABq, B-part, J=9.6 Hz, 1H), 4.75~4.90(m, 2H). 5.74(s,1H), 7.35~7.65(m,5H).

IR(Nujol)νmax: 3680~2200, 1733, 1710(sh), 1230, 1177, 1044, 994, 925, 819, 724 cm$^{-1}$.

$[α]_D$ −92.0°±1.3° (MeOH, 23° C., C=1.014%).

EXAMPLE 23

Preparation of (1R,2R,3R,4S)-7-oxabicylo[2.2.1]heptan-2,3-dicarboxylic acid, 2-methyl ester III-3-D-1

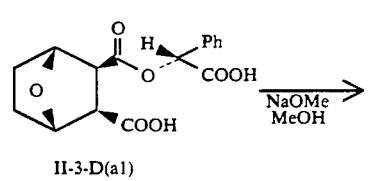

II-3-D(a1)

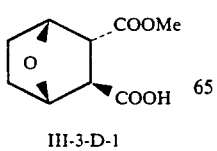

III-3-D-1

According to the procedure in Example 17, 190 mg of the compound III-3-D-1 was prepared from 610 mg (1.9 mmol) of the compound II-3-D(a1) in 50.0% yield.

mp. 134°–135° C.

Anal. Calcd. (%) for $C_9H_{12}O_5$: C, 54.00; H, 6.05; Found (%):C, 53.98; H, 5.97.

$^1$HNMR($CDCl_3$-TMS)δppm: 1.45~1.95(m,4H), 3.14(d, J=5.1 Hz, 1H), 3.50(t-d, J=5.5, 1.5 Hz, 1H), 3.74(s, 3H), 4.84(t, J=5.0 Hz, 1H), 4.92(d, J=5.0 Hz, 1H).

IR(Nujol)νmax: 3400~2480, 1736, 1725, 1255, 1215, 1201, 1184, 1173, 921, 816 cm$^{-1}$.

$[α]_D$ +73.3°±0.6° (MeOH, 24° C., C=2.009%).

EXAMPLE 24

Preparation of (1S, 2S, 3S, 4R)-7-oxabicylo[2.2.1]heptan-2,3-dicarboxylic acid, 2-methyl ester III-3-L-1

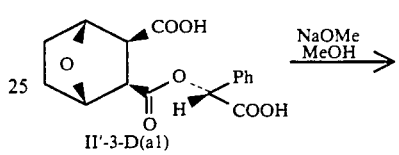

II'-3-D(a1)

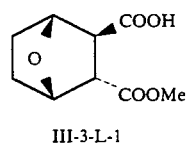

III-3-L-1

According to the above mentioned procedure, the compound III-3-L-1, enantiomer of the compound III-3-D-1, was prepared from the by-product of the cleavage reaction, i.e. the compound II-3-D(a1) in 27.5% yield.

mp. 133°–134° C.

Anal. Calcd. (%) for $C_9H_{12}O_5$: C, 54.00; H, 6.05; Found (%): C, 54.03; H, 6.06.

The $^1$HNMR and IR data were identical with those of the compound III-3-D-1, respectively.

$[α]_D$ −73.5°±0.6° (MeOH, 23° C., C=2.013%).

EXAMPLE 25

Preparation of (1S, 2R, 3S, 4R)-7-oxabicyclo[2.2.1]heptan-2,3-dicarboxylic acid, 2-methyl ester III-3-D-2

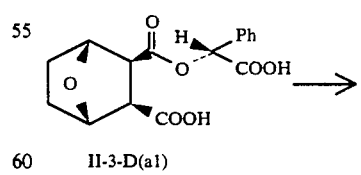

II-3-D(a1)

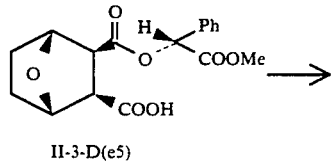

II-3-D(e5)

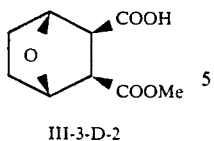

III-3-D-2

By a usual manner, 4.5 g (14.05 mmol) of the compound II-3-D(a1) was treated with a solution of diazomethane in ether to give 4.77 g of the compound II-3-D(e5) in 97.5% yeild.

Dimethyl ester II-3-D(e5)

mp. 131°–132° C.

Anal. Calcd. (%) for $C_{18}H_{20}O_7$: C, 62.05; H, 5.80; Found (%): C, 61.87; H, 5.78.

$^1$HNMR(CDCl$_3$-TMS)δppm: 1.45~1.70(m,2H), 1.77~1.93(m,2H), 2.99(ABq, A-part, J=9.6 Hz, 1H), 3.15(ABq, B-part, J=9.6 Hz, 1H), 3.53(s, 3H), 3.70(s, 3H), 4.85~4.93(m, 1H), 4.95~5.03 (m, 1H), 5.93(s, 1H), 7.34~7.55(m, 5H).

IR(Nujol)νmax: 1742, 1732, 1198, 1143, 1055, 1009, 936, 725, 695 cm$^{-1}$.

$[α]_D$ −103.2°±1.4° (CHCl$_3$, 23.5° C., C=1.009%).

To a solution of 4.18 g (12 mmol) of dimethyl ester II-3-D(e5) in 30 ml of ethyl acetate is added 400 mg of 10% Pd-C and the mixture was stirred for 1 hour in a hydrogen atmosphere. The catalyst was removed by filtration and the filtrate was concentrated under reduced pressure. The residue was recrystallized from ether to give 2.02 of the cis-half ester III-3-D-2 in 84.2% yield.

mp. 104°–106° C.

Anal. Calcd. (%) for $C_9H_{12}O_5$: C, 54.00; H, 6.05; Found (%): C, 53.83; H, 6.04.

$^1$HNMR(CDCl$_3$-TMS)δppm: 1.45~1.60(m, 2H), 1.73~1.93(m, 2H), 3.01(ABq, A-part, J=9.6 Hz, 1H), 3.03(ABq, B-part, J=9.6 Hz, 1H), 3.66(s, 3H), 4.87~5.03(m, 2H), 6.56(br.s, 1H).

IR(Nujol)νmax: 3400~2480, 1736, 1731, 1228, 1198, 1169, 1010, 996, 924, 900, 821 cm$^{-1}$.

$[α]_D$ −4.9°±0.2° (MeOH, 23.5° C., C=2.010%).
$[α]_{365}$ −7.9°±0.2° (MeOH, 23.5° C., C=2.010%).

This product had the nearly same $[α]_D$ value of the compound III-3-D-2 reported by R. Bloch et al. (Tetrahedron Letters, 26, No. 34, pp. 4087–4090 (1985) ($[α]_D$ −3.9° (MeOH, 20° C., C=2%), mp. 104° C.)).

EXAMPLE 26

Preparation of (1R,2S,3R,4S)-7-oxabicyclo[2.2.1]heptan-2,3-dicarboxylic acid, 2-methyl ester III-3-L-2

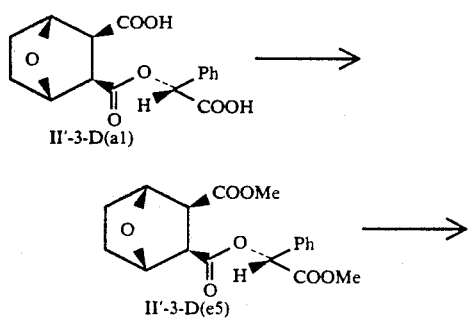

II'-3-D(a1)

II'-3-D(e5)

III-3-L-2

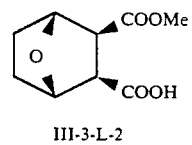

According to the procedure by which the compound II-3-D(e5) was prepared from the compound II-3-D(a1), the reaction was conducted using 720 mg (2.25 mmol) of the by-product II'-3-D(a1) of the cleavage reaction to give 678 mg of the compound II'-3-D(e5) in 86.6% yield.

Dimethyl ester II'-3-D(e5)

mp. 115°–116° C.

Anal. Calcd. (%) for $C_{18}H_{20}O_7$: C, 62.05; H, 5.80; Found (%): C, 61.85; H, 5.74.

$^1$HNMR(CDCl$_3$-TMS)δppm: 1.45~1.70(m, 2H), 1.74~1.95(m, 2H), 2.97(ABq, A-part, J=9.6 Hz, 1H), 3.17(ABq, B-part, J=9.6 Hz, 1H), 3.36(s, 3H), 3.71(s, 3H), 4.84~4.95(m, 1H), 5.00~5.10(m, 1H), 5.89(s, 1H), 7.33~7.50(m, 5H).

IR(Nujol)νmax: 1753, 1737, 1725, 1220, 1190, 1164, 1145, 1056, 1028, 1004, 817, 735, 693 cm$^{-1}$.

$[α]_D$ −84.7°±1.2° (CHCl$_3$, 23° C., C=1.008%).

According to the procedure by which the compound III-3-D-2 was prepared from the compound II-3-D(e5), the reaction was conducted using 523 mg (1.5 mmol) of dimethyl ester II'-3-D(e5) to give 271 mg of the cis-half ester III-3-L-2 in 90.3% yield.

mp. 103°–105° C.

Anal. Calcd. (%) for $C_9H_{12}O_5.0.1H_2O$: C, 53.51; H, 6.10; Found (%) C, 53.67; H, 5.90.

The $^1$HNMR and IR data were identical with those of the compound III-3-D-2, respectively.

$[α]_D$ +4.4°±0.2° (MeOH, 24° C., C=2.006%).
$[α]_{365}$ +7.0°±0.2° (MeOH, 24° C., C=2.006%).

EXAMPLE 27

Preparation of (1R,2R,3S,4S)-2-(methyl-D-mandeloxycarbonyl)-3-methoxycarbonylbicyclo[2.2.1]heptane II-2-D(e5)

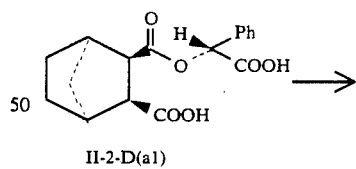

II-2-D(a1)

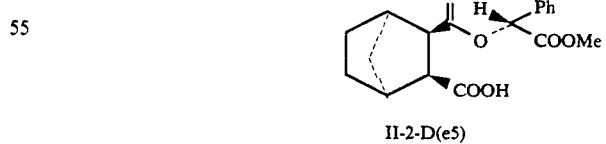

II-2-D(e5)

A mixture of 22.72 g (71.3 mmol) of the compound II-2-D(a1) and 2.73 g (14.3 mmol) of p-toluenesulfonic acid mono-hydrate in 375 ml of methanol was refluxed for 24 hours. The reaction mixture was concentrated and the residue was partitioned between 5% aqueous sodium hydrogencarbonate and ethyl acetate. The organic layer was washed with water, dried, and concentrated to give 26.06 of the crude aimed product, which was recrystallized from ether/petroleum ether to give 18.59 g (53.7 mmol) as first crop, 0.62 g (1.8 mmol) as second crop, and 0.53 g (1.5 mmol) as third crop (total isolated yield: 19.74 g (yield; 79.9%) of the aimed compound II-2-D(e5).

mp. 61.5°–63.5° C.

Anal. Calcd. (%) for $C_{19}H_{22}O_6$: C 65.88, H 6.40; Found (%): C 65.72, H 6.42.

IR(KBr)νmax: 3700~3160, 2970, 2885, 1758, 1745, 1730, 1457, 1365, 1345, 1198, 1165, 1122, 1082, 1060, 1055, 1042, 1022, 748, 698 cm$^{-1}$.

$^1$HNMR(CDCl$_3$-TMS)δppm: 1.20~2.00(m,6H), 2.50~2.65(brm,2H), 2.96(dABq, A-part, J=3.8, 11.8 Hz), 3.21(dABq, B-part, J=4.3, 11.8 Hz), 3.54(s,3H), 3.70(m,3H), 5.94(s,1H), 7.30~7.52(m,5H).

$[\alpha]_D - 77.8° \pm 1.2°$ (CHCl$_3$, 23.5° C., C=1.00%).

EXAMPLE 28

Preparation of (1S,2S,3R,4R)-bicyclo[2.2.1]heptan-2,3-dicarboxylic acid, 2-methyl ester III-2-D-2

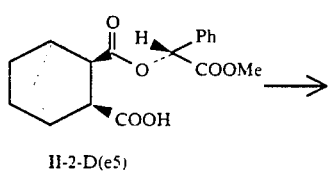

To 1.77 g of 10% palladium-carbon was added a solution of 17.79 g (51.4 mmol) of the compound II-2-D(e5) in 200 ml of ethyl acetate and the mixture was stirred for 50 minutes at room temperature under hydrogen atmosphere. The catalyst was removed by filtration and the filtrate was concentrated. Toluene and 5% aqueous sodium hydrogencarbonate were added to the residue and the aqueous layer was separated. The organic layer was extracted with water again. Each aqueous layer was washed with toluene and the combined aqueous layer was acidified with 2N hydrochloric acid and extracted with ethyl acetate. The organic layer was washed with water, dried, and concentrated to give 10.2 g of the aimed compound III-2-D-2 quantitatively.

Anal. Calcd. (%) for $C_{10}H_{14}O_4$: C 60.59, H 7.12; Found (%): C 60.42, H 7.05.

IR(KBr)νmax: 3400~2400, 2960, 2880, 1735, 1708, 1435, 1356, 1295, 1288, 1132, 1122, 1082, 1058 cm$^{-1}$.

$^1$HNMR(CDCl$_3$-TMS)δppm: 1.35~1.53(m,4H), 1.65~1.88(m,2H), 2.48~2.64(brm,2H), 2.96(dABq, A-part, J=3.4, 11.7 Hz, 1H), 3.03(dABq, B-part, J=4.4, 11.7 Hz, 1H), 3.64(s,3H).

$[\alpha]_D + 17.1° \pm 0.3°$ (MeOH, 23.0° C., C=2.059%).

EXAMPLE 29

Preparation of (1S,2S,3R,4R)-2-(methyl-L-mandeloxycarbonyl)-3-methoxycarbonylbicyclo[2.2.1]heptane II-2-L(e5)

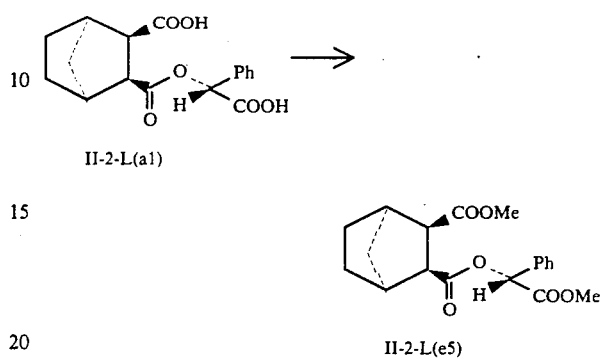

According to the procedure in Example 27, the reaction was conducted using the compound II-2-L(a1) to give the compound II-2-L(e5) in yield 87.5%.

mp. 65.1°–62.5° C.

$[\alpha]_D + 76.3° \pm 1.2°$ (CHCl$_3$, 24° C., 1.005%).

EXAMPLE 30

Preparation of (1R,2R,3S,4S)-bicyclo[2.2.1]heptan-2,3-dicarboxylic acid, 2-methyl ester III-2-L-2

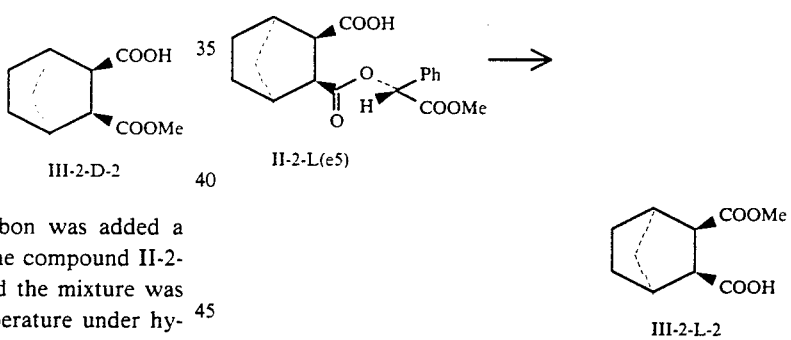

By the same manner as in Example 28, the reaction was subjected to give the aimed compound III-2-L-2 quantitatively.

$[\alpha]_D - 17.4° \pm 0.3°$ (MeOH, C=2.052%, 24° C.).

Referential Example 1

Processes for Preparing Arylacetic Acid Derivatives (1) Benzyl D-mandelate

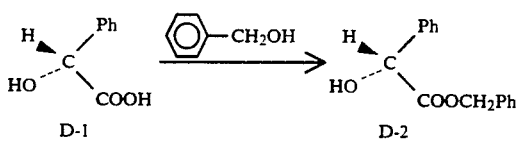

A solution of 85.1 g (559 mmol) of D-mandelic acid, 65 ml (628 mmol) of benzyl alcohol, and 1.01 g (5.35 mmol) of p-toluenesulfonic acid in 700 ml of benzene was refluxed for 6.5 hours. The mixture was washed with water and concentrated. The residue was recrystallized from ether to give 123.5 g of the aimed compound D-2 in 91% yield.

Mp. 103.5°–105° C.

Anal. Calcd. (%) for $C_{15}H_{14}O_3$: C, 74.36; H, 5.82; Found (%): C,74.53; H,5.90.

$^1$H-NMR(CDCl$_3$-TMS) δppm: 3.44(d, J=5.6 Hz, 1H), 5.14(ABq, Apart, J=12.3 Hz, 1H), 5.22(d,J=5.6 Hz, 1H), 5.24(ABq, Bpart, J=12.3 Hz, 1H)7.15~7.50(m, 10H).

$[α]_D = -55.7 \pm 1.0$ (CHCl$_3$, C=1.003%, 24° C.).

(2) 4-Methoxybenzyl D-madelate

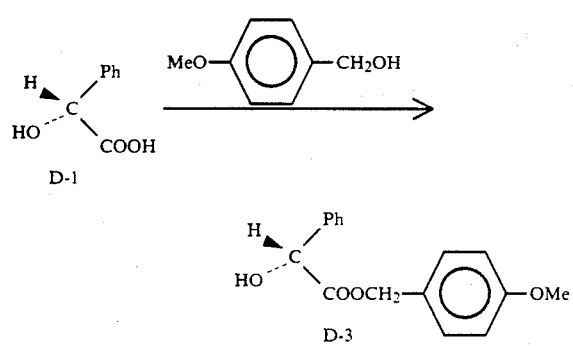

A solution of 15.3 g (100 mmol) of D-mandelic acid, 15.2 g (110 mmol) of 4-methoxybenzyl alchohol, and 0.197 g (1.01 mmol) of p-toluenesulfonic acid in 300 ml of benzene was refluxed for 7 hours. The mixture was washed with water 4 times and concentrated. The residue was purified by column chromatography on silica gel eluted with toluene-ethyl acetate and then by recrystallization from ether-petroleum ether to give 6.58 g of the aimed compound D-3 in 24% yield.

Mp. 70.5°–73.5° C.

Anal. Calcd. (%) for $C_{16}H_{16}O_4$: C, 70.58; H, 5.92; Found (%): C, 70.55; H, 6.00.

$^1$H-NMR(CDCl$_3$-TMS) δ ppm: 3.80(s, 3H), 5.05(ABq, Apart, J=11.8 Hz, 1H), 5.19(s, 1H), 5.19(ABq, Bpart, J=11.8 Hz, 1H), 6.84(d, J=8.7 Hz, 2H), 7.17(d, J=8.7 Hz, 2H), 7.30~7.45(m, 5H).

$[α]_D = -36.0° \pm 0.8°$ (CHCl$_3$, C=1.017%, 24° C.).

(3) 4-Nitrobenzyl D-mandelate

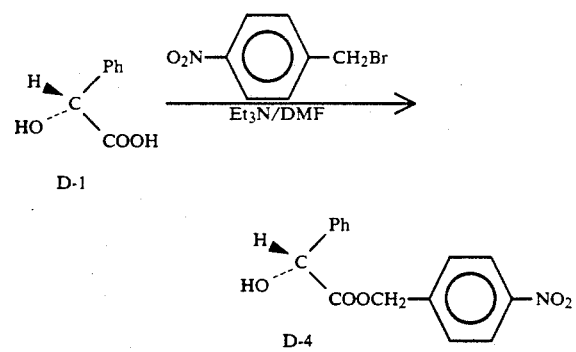

A solution of 15.2 g (100 mmol) of D-mandelic acid, 21.6 g (100 mmol) of 4-nitrobenzyl bromide, and 14.0 ml (100 mmol) of triethylamine in 300 ml of DMF was stirred for 8 hours at room temperature. Water was added to the reaction mixture and the mixture was extracted with ethyl acetate. The organic layer was washed with 2N hydrochloric acid and water and recrystallized from ether-petroleum ether to give 19.6 g of the aimed product D-4 in 68% yield.

Mp. 143°~145° C.

Anal. Calcd. (%) for $C_{15}H_{13}NO_5$: C, 62.72; H, 4.56; N, 4.88; Found (%): C, 62.76; H, 4.61; N, 4.99.

$^1$H-NMR(CDCl$_3$-TMS)δppm: 3.26~3.52(br. s, 1H), 5.25(ABq, Apart, J=13.5 Hz, 1H), 5.28(s,1H), 5.32(ABq, Bpart, J=13.5 Hz, 1H), 7.27(d, J=8.4 Hz, 2H), 7.34~7.48(br. s, 5H), 8.14(d, J=8.4 Hz, 2H).

$[α]_D = -40.0° \pm 0.8°$ (CHCl$_3$, C=0.995%, 24° C.).

(4) Benzhydryl D-mandelate

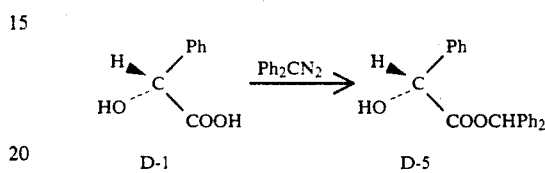

To a solution of 25.0 g (164 mmol) of D-mandelic acid in 200 ml of ethyl acetate was added 38.9 g (164 mmol) of diphenyldiazomethane under stirring at room temperature. The completeness of reaction was monitored by TLC and the reaction mixture was concentrated. The residue was recrystallized from etherpetroleum ether to give 47.7 g of the aimed product D-5 in 91% yield.

Mp. 91°–91.5° C.

Anal. Calcd. (%) for $C_{21}H_{18}O_3$: C, 79.22; H, 5.71; Found (%): C, 79.44; H, 5.67.

$^1$H-NMR(CDCl$_3$-TMS)δppm: 3.47(d, J=5.3 Hz), 5.28(d, J=5.3 Hz, 1H), 6.87(s, 1H), 6.87~7.46(m, 15H) $[α]_D = -57.4° \pm 1.0°$ (CHCl$_3$, C=1.023%, 24° C.)

(5) Benzhydryl L-mandelate

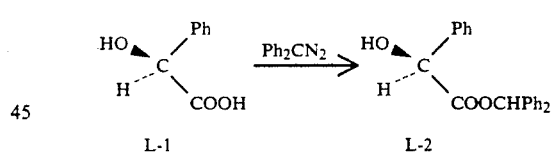

According to the procedure in Referential Example 1-(4), the desired compound was obtained by reacting 30.4 g (200 mmol) of L-mandelic acid with 38.9 g (200 mmol) of diphenyldiazomethane in 200 ml of ethyl acetate to give 54.7 g (172 mmol) of the compound L-2 in 86% yield. Mp. 91.5°–92.0° C. $[α]_D = +55.7 \pm 0.9°$ (CHCl$_3$, C=1.013%, 24° C.).

REFERENTIAL EXAMPLE 2

A use of the compound (III) prepared in this invention was exemplified as follows.

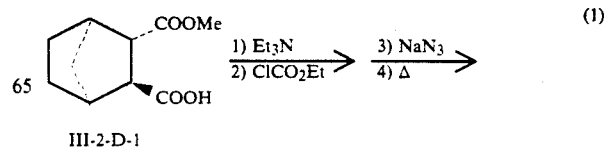

(1)

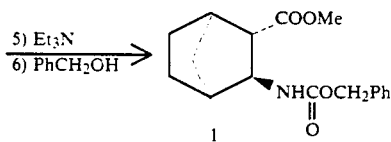

In a nitrogen atmosphere, a solution of 2.80 g (14.1 mmol) of the compound III-2-D-1 in 24 ml of acetone was cooled to 0° C. and 2.54 ml (18.3 mmol) of triethylamine and 1.75 ml (18.3 mmol) of ethyl chlorocarbonate were added thereto. Then, colorless solids were precipitated immediately. The mixture was stirred for 15 minutes and a solution of 2.75 g (42.3 mmol) of sodium azide in 8 ml of water was added. The mixture was stirred under ice-cooling and acidified with 2N hydrochloric acid. The resulting mixture was extracted with ethyl acetate and the organic layer was washed with water and then with an aqueous solution of sodium chloride and concentrated. Benzene was added to the residue and concentrated again in order to remove ethyl acetate completely.

The resulting oil was dissolved in 20 ml of benzene and the mixture was heated to 80° C. to perform thermal rearrangement. When the evolution of nitrogen gas has ceased, 2.54 ml (18.3 mmol) of triethylamine and 1.75 ml (16.9 mmol) of benzyl alcohol were added and the resulting mixture was refluxed for 1.5 hours. After the reaction was finished, 2N hydrochloric acid was added to the reaction mixture which was then extracted with ethyl acetate. The organic layer was washed with water, and then with aqueous solution of sodium chloride and concentrated. The crude product was purified by column chromatography on silica gel and recrystallized to give 3.03 g of the compound 1 in 71% yield.

Mp.: 61°–62° C.

Anal. Calcd. (%) for $C_{17}H_{21}NO_4$: C, 67.30; H, 6.99; N, 4.62; Found (%): C,67.46; H,7.04; N,4.73.

$^1$H-NMR(CDCl$_3$-TMS)δppm: 1.22~1.86(m, 6H), 1.92 (dd, J=2.0, 5.0 Hz, 1H), 2.50(br. s, 2H),3.70(br. s, 3H), 4.23(br. s, 1H), 4.90(br. s, 1H), 5.09(br. s, 2H), 7.22~7.45(m, 5H).

$[\alpha]_D = +40.1°\pm 0.4°$ (CHCl$_3$, c=2.006, 25° C.).

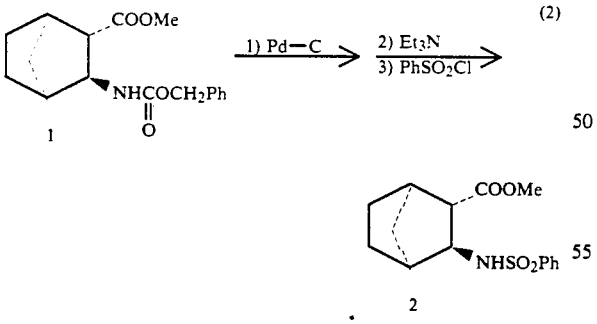

To a solution of 1.42 g (4.67 mmol) of the compound 1 in 13 ml of methanol was added 0.130 g of 10% palladium-carbon and the mixture was stirred in a hydrogen atomsphere under ordinally pressure at room temperatuer for 30 minutes. The catalyst was removed by filtration and filtrate was concentrated.

In a nitrogen atmosphere, a mixture of the prepared crude product in 10 ml of dichloromethane was cooled to 0° C. and 1.94 ml (14.0 mmol) of triethylamine and 0.66 ml (5.17 mmol) of benzenesulfonyl chloride were added thereto. The mixture was stirred for 30 minutes. The reaction mixture was acidified with 2N hydrochloric acid and then extracted with ethyl acetate. The organic layer was washed with water and a saturated aqueous solution of sodium chloride and concentrated. The residue was purified by column chromatography on silica gel to give 1.17 g of the aimed compound 2 in 81% yield.

Mp. 129°–130° C.

Anal. Calcd. (%) for $C_{15}H_{19}NO_4S$: C, 58.22; H, 6.20; N, 4.52; S, 10.36; Found (%): C, 58.11; H, 6.07; N, 4.53; S, 10.09.

$[\alpha]_D = -0.4°\pm 0.4°$ (CHCl$_3$, C=0.992%, 25° C.).

$[\alpha]_{365} = -36.2°\pm 0.8°$ (CHCl$_3$, C=0.992%, 25° C.).

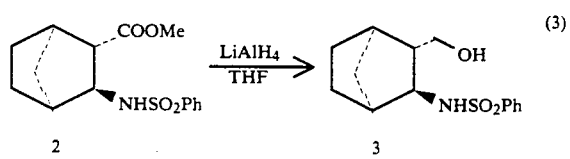

In a nitrogen atmosphere, 0.412 g (10.9 mmol) of lithium aluminum hydride was added to a solution of 1.12 g (3.62 mmol) of compound 2 in 15 ml of THF at room temperature and the mixture was stirred for 30 minutes. In order to decompose the remaining lithium aluminum hydride, ethyl acetate and water were added to the reaction mixture, successively. The mixture was extracted with ethyl acetate (three times) and the organic layer was concentrated to give 1.00 g of the aimed compound in 98.2% yield.

Mp. 121°–122° C.

Anal. Calcd. (%) for $C_{14}H_{19}NO_3S$: C, 59.75; H, 6.82; N, 4.98; S, 11.39: Found (%): C, 59.83; H, 6.91; N, 5.02; S, 11.33.

$[\alpha]_D = +6.8°\pm 0.5°$ (CHCl$_3$, C=1.000%, 26° C.).

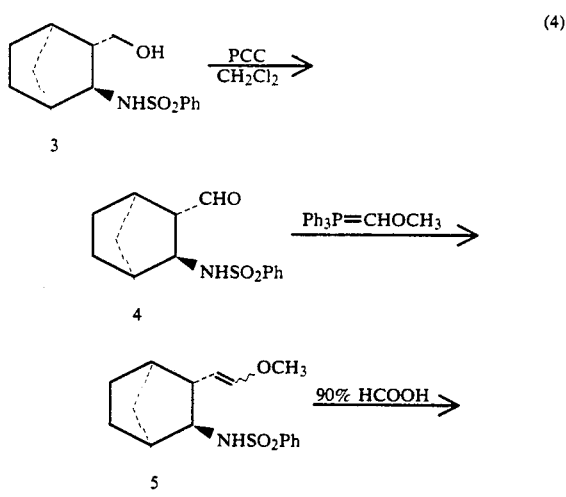

In a nitrogen atmosphere, 18.4 g (85.4 mmol) of PCC and 25.1 g of molecular sieves (4A powder) were added to a solution of 8.01 g (28.5 mmol) of the compound 3 in 600 ml of dichloromethane and the mixture was stirred at room temperature. The completeness of the reaction was monitored by TLC and the inorganic substances were removed by column chromatography on silica gel. The eluate was concentrated to give the intermediate 4. Without further purification, the intermediate was subjected to next reaction, since it was not so stable.

In a nitrogen atmosphere, 56.0 ml (84.0 mmol) of n-butyl lithium (1.6M in hexane) was added to a suspension of 31.20 g (91.0 mmol) of methoxymethyltriphenylphosphonium chloride in 160 ml of THF at −78° C. After addition, a dry ice bath was changed to an ice bath and the mixture was stirred for 25 minutes at 0° C. The reaction mixture was cooled to −78° C. again in dry ice-acetone bath and a solution of 7.27 g of the above intermediate 4 in 80 ml of THF was added dropwise thereto. After addition, the ice bath was removed and the mixture was stirred for 35 minutes. Ice-water was added to the reaction mixture, which was extracted with ethyl acetate. The organic layer was washed with water and a saturated aquoues solution of sodium chloride and then concentrated. The residue was chromatographed on silica gel to give the intermediate 5, which was subjected to next reaction without further purification, as it was also unstable.

In a nitrogen atmosphere, 5.0 ml of 90% formic acid was added to 5.86 g of the compound 5 and the mixture was stirred for 1 hour at room temperature. The reaction was monitored by TLC and then the reaction mixture was neutralized with an aquoues solution of sodium hydrogencarbonate. Water was added to the mixture, which was extracted with ethyl acetate. The organic layer was washed with water and a saturated aqueous solution of sodium chloride and concentrated. The residue was purified by column chromatography on silica gel to give 3.30 g of the aimed compound 6 in 40% yield from the compound 3.

Compound 6

Mp. 100°–103° C.

Anal. Calcd. (%) for $C_{15}H_{19}NO_3S$: C, 61.40; H, 6.54; N, 4.77; S, 10.93; Found (%): C, 61.39; H, 6.51; N, 4.90; S, 11.02. $[\alpha]_D = +36.5° \pm 0.8°$ (CHCl$_3$, C=0.994%, 25.5° C.).

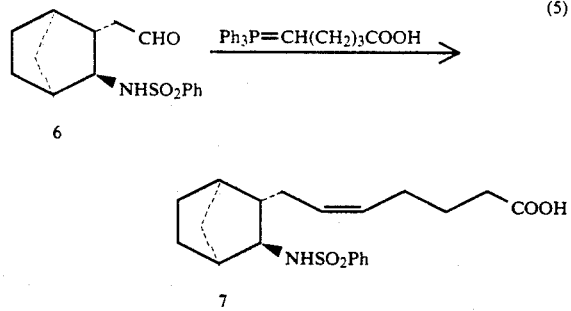

In a nitrogen atmosphere, 7.55 g (67.3 mmol) of potassium t-butoxide was added to a suspension of 14.8 g (33.3 mmol) of 4-carboxylbutyltriphenylphosphonium bromide in 80 ml of THF at room temperature and the mixture was stirred for 1 hour at room temperature and then cooled to −20° C.

A solution of 3.25 g (11.1 mmol) of the compound 6 in 20 ml of THF was added slowly to the above mixture and the mixture was stirred for about 1.5 hour at −20° C. and stirred for additional one hour without an ice bath. The reaction mixture was acidified with 2N hydrochloric acid and extracted with ethyl acetate. The extract was washed with water and a saturated aquoues solution of sodium chloride and then concentrated. The prepared curde product was partitioned between toluene and 1N sodium hydroxide and the aqueous layer was separated. The organic layer was extracted with water again. The combined aqueous layer was acidified with 2N hydrochloric acid and extracted with ethyl acetate. The organic layer was washed with water and a saturated aquoue solution of sodium chloride, dried over sodium sulfate, and concentrated. The residue was purified by column chromatography on silica gel to give 3.29 g of the aimed compound 7 in 79% yield.

Mp. 62° C.

Anal. Calcd. (%) for $C_{20}H_{27}NO_4S$: C, 63.63; H, 7.21; N, 3.71; S, 8.49; Found (%): C, 63.56; H, 7.21; N, 3.83; S, 8.43.

$[\alpha]_D = +5.3° \pm 0.5°$ (CHCl$_3$, C=1.003%, 22° C.).
$[\alpha]_D = +27.1° \pm 0.7°$ (MeOH, C=1.015%, 24° C.).

REFERENTIAL EXAMPLE 3

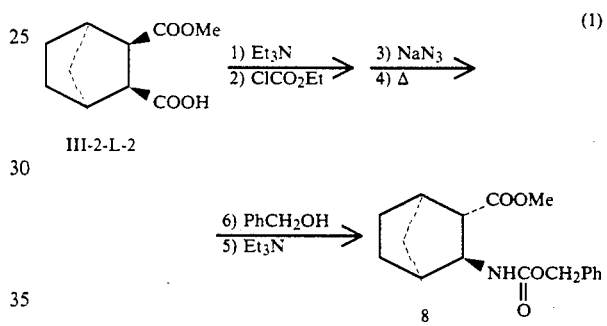

In a nitrogen atmosphere, a solution of 5.00 g (25.2 mmol) of the compound III-2-L-2 in 25 ml of acetone was cooled to 0° C. and 3.90 ml (28.0 mmol) of triethylamine and 2.65 ml (27.7 mmol) of ethyl chlorocarbonate were added thereto. Then, colorless solids were precipitated immediately. The mixture was stirred for 30 minutes and 6 ml of aqueous solution of 1.72 g (26.5 mmol) of sodium azide was added. The mixture was stirred for 45 minutes under ice-cooling and acidified with 2N hydrochloric acid. The resulting mixture was extracted with ethyl acetate and the organic layer was washed with 5% aqueous solution of sodium hydrogen-carbonate, water, and an aqueous solution of sodium chloride, dried, and concentrated. Benzene was added to the residue and concentrated again in order to remove ethyl acetate completely.

The resulting oil was dissolved in 25 ml of benzene and the mixture was heated to perform thermal rearrangement. When the evolution of nitrogen gas has ceased, 2.75 ml (26.5 mmol) of benzyl alcohol and 3.90 ml (28.0 mmol) of triethylamine were added and the resulting mixture was refluxed for 75 minutes. After the reaction was finished, 2N hydrochloric acid was added to the reaction mixture which was then extracted with ethyl acetate. The organic layer was washed with 5% aqueous solution of sodium hydrogencarbonate, water, and an aqueous solution of sodium chloride and concentrated. The crude product was purified by column chromatography on silica gel with toluene-ethyl acetate to give 3.99 g (13.2 mmol) of the aimed compound 8 in 52.1% yield.

Anal. Calcd. (%) for $C_{17}H_{21}NO_4$: C, 67.31; H, 6.98; N, 4.62; Found (%): C,67.12; H,6.96; N,4.63.

IR(CHCl$_3$)$\nu$max: 3400, 2950, 2880, 1718, 1505, 1453, 1438, 1358, 1325, 1316, 1163, 1152, 1080, 1062, 1035, 1028 cm$^{-1}$.

$^1$H-NMR(CDCl$_3$-TMS)$\delta$ppm: 1.32~1.70(m, 6H), 2.49(br. s, 2H), 2.93(dd,J=4.3 Hz, J=11.1 Hz, 1H), 3.63(s, 3H), 3.97~4.18(m, 1H), 5.08(s, 2H), 6.65~6.83(br.m, 1H), 7.28~7.44(m, 5H).

$[\alpha]_D$ = +6.1°±0.5° (CHCl$_3$, C=1.010%,23.5° C.)
$[\alpha]_{365}$ = +28.5°±0.7° (CHCl$_3$, 3,C=1.010%,23.5° C.)

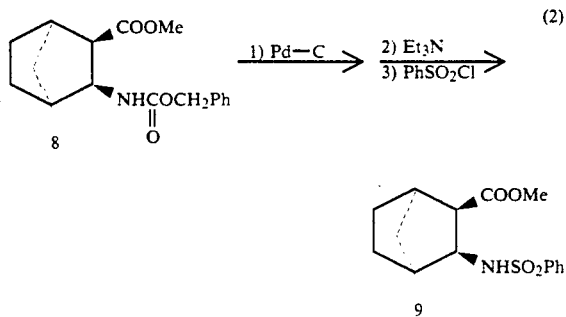

(2)

To a solution of 3.87 g (12.8 mmol) of the compound 8 in 15 ml of methanol was added 0.602 g of 10% palladium-carbon and the mixture was stirred in a hydrogen atmosphere under ordinally pressure at room temperature for 100 minutes. The catalyst was removed by filtration and the filtrate was concentrated.

In a nitrogen atmosphere, a mixture of the prepared crude product in 10 ml of dichloromethane was cooled to 0° C. and 3.60 ml (25.8 mmol) of triethylamine and 1.66 ml (13.0 mmol) of phenylsulfonyl chloride were added thereto. The mixture was stirred for 30 minutes. The reaction mixture was acidified with 2N hydrochloric acid and then extracted with ethyl acetate. The organic layer was washed with 5% aqueous solution of sodium hydrogencarbonate, water, and a saturated aqueous solution of sodium chloride and concentrated. The residue was purified by column chromatography on silica gel to give 3.20 g (10.3 mmol) of the aimed compound 9 in 81.0% yield.

m.p. 112.5°-113.5° C.

Anal. Calcd. (%) for $C_{15}H_{19}NO_4S$: C, 58.23; H, 6.19; N, 4.53; S,10.36 Found (%): C,58.33; H,6.19; N,4.45; S,10.08.

IR(KBr)$\nu$max: 3335, 3270, 2965, 2880, 1705, 1445, 1435, 1368, 1352, 1330, 1202, 1165, 1092, 905, 758, 732, 725, 690, 667, 586, 552 cm$^{-1}$.

$^1$H-NMR(CDCl$_3$-TMS)$\delta$ppm: 1.22~1.76(m, 6H), 2.30(br. s, 1H), 2.43(br. s, 1H), 2.64(dd,J=4.8 Hz, J=10.6 Hz,1H), 3.51(s, 3H), 3.66~3.82 (m, 1H), 6.74(d,J=8.8 Hz,1H), 7.42~7.51(m, 3H), 7.77~7.90(m, 2H).

$[\alpha]_D$ = −42.1±0.8° (CHCl$_3$,C=1.002%,24° C.).

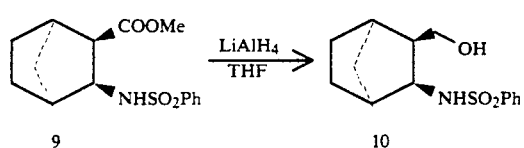

(3)

In a nitrogen atmosphere, to a suspension of 1.54 g of lithium aluminum hydride in 30 ml of THF was added a solution of 3.00 g (9.70 mmol) of compound 9 in 30 ml of THF and the mixture was stirred for 2 hour. In order to decompose the remaining lithium aluminum hydride, ethyl acetate and water were added to the reaction mixture, successively. The mixture was extracted with ethyl acetate (three times) and the organic layer was concentrated to give 2.70 g of the aimed compound 10 in 99.0% yield.

mp. 97.5°-99.5° C.

Anal. Calcd. (%) for $C_{14}H_{19}NO_3S$: C, 59.76; H, 6.81; N, 4.98; S,11.39; Found (%): C,59.68; H,6.77; N,4.92; S,11.14.

IR(KBr)$\nu$max: 3640~3360, 3260, 2960, 2890,1482, 1463, 1448, 1340, 1310, 1165, 1155, 1092, 1046, 955, 755, 718, 688, 595, 575, 549 cm$^{-1}$.

$^1$H-NMR(CDCl$_3$-TMS)$\delta$ppm: 1.16~2.27(m, 10H), 3.40~3.56(m, 1H), 3.62(dABq, Apart, J=5.0, 11.0Hz,1H), 3.81(dABq, Bpart, J=9.0, 11.0 Hz,1H), 5.51~5.78(br.m, 1H), 7.46~7.70(m, 3H), 7.85~8.00(m, 2H).

$[\alpha]_D$ = +35.1°±0.8° (CHCl$_3$, C=1.005%, 24.0° C.).

The racemate of the compound 10 can be separated into (+)-isomer and (−)-isomer by HPLC using chiral column. (ULTRON ES-OVM)

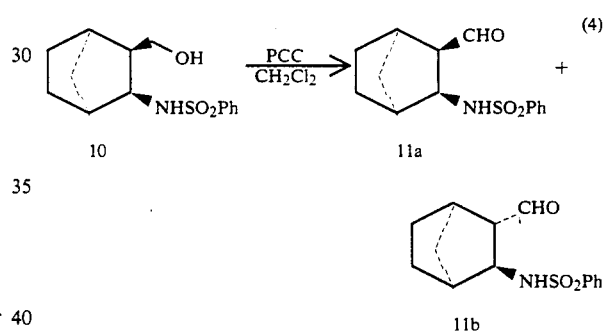

(4)

In a nitrogen atmosphere, to a suspension of 0.700 g (3.25 mmol) of PCC and 0.703 g of molecular sieves (4A powder) in 15 ml of dichloromethane was added a solution of 0.304 g (1.08 mmol) of the compound 10 in 5 ml of dichloromethane under ice-cooling. The mixture was stirred for 45 minutes at 0° C. and additional 45 minutes at 30° C. The completeness of the reaction was monitored by TLC and the inorganic substances were removed by passing through silica gel. The eluate was concentrated to give the mixture of the compounds 11a and 11b quantitatively. (11a:11b=9:1). Since the compound 11a was not so stable, it was gradually converted into the compound 11b during the isolation procedure.

$^1$H-NMR(CDCl$_3$-TMS)$\delta$ppm: 2.58~2.66(br.m, 1H), 2.74~2.88(m, 1H), 3.64~3.78(d,J=7.5 Hz, 1H), 9.49(s, 1H). (Only the characteristic signals for the compound 11a are shown.)

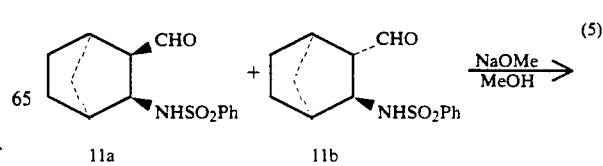

(5)

-continued

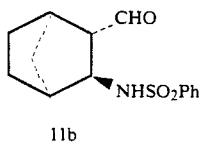
11b

In a nitrogen atmosphere, 1.0 ml (0.200 mmol) of 0.2N sodium methoxide in methanol was added to a solution of 0.551 g (1.97 mmol) of the mixture of the compounds 11a and 11b in 3.0 ml of methanol of and the resulting mixture was stirred for 60 minutes at room temperature. The completeness of the reaction was monitored by TLC. The reaction mixture was concentrated and the residue was partitioned between 2N hydrochloric acid and ethyl acetate. The organic layer was washed with water and a saturated aqueous solution of sodium chloride, dried, and concentrated to give 0.537 g of the aimed compound 11b in 97.5% yield.

mp. 100°–103° C.

Anal. Calcd. (%) for $C_{14}H_{17}NO_3S$: C, 60.19; H, 6.13; N, 5.01; S,11.48; Found (%): C,60.08; H,6.09; N,5.11; S,11.41.

IR(KBr)$\nu$max: 3250, 2960, 2940, 1712, 1462, 1448, 1338, 1325, 1158, 1145, 1128, 1090, 1080, 753, 720, 682, 655, 590, 542 cm$^{-1}$.

$^1$H-NMR(CDCl$_3$-TMS)$\delta$ppm: 1.05~1.85(m, 6H), 2.18~2.31(m, 2H), 2.45(d, J=3.6 Hz, 1H), 3.81~3.94(m,1H), 4.90~5.05(br.m,1H), 7.40~7.67(m,3H), 7.76~7.97(m, 2H), 9.55(s,1H).

$[\alpha]_D = -47.6° \pm 0.9°$ (CHCl$_3$, C=1.009%, 24.0° C.).

The compound 11b thus prepared is identified with the compound 4 prepared in Referential Example 2 (4). So it can be converted into the compound 7 by the same procedure as in Referential Examples 2 (4) and (5).

We claim:

1. A pure optically active mono-ester of the following formula:

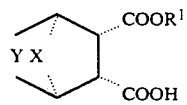

wherein X is —CH$_2$—; Y is —(CH$_2$)$_2$ or —CH=CH— and wherein R$^1$ is alkyl which may be substituted by alkoxy, halogen, amino, hydroxyamino, alkylamino, or nitro or R$^1$ is alkenyl, aryl or aralkyl, each of which may be substituted by alkyl, alkoxy, halogen, amino, hydroxyamino, alkylamino or the enantiomer of said carboxylic acid esters of the aforementioned formula.

* * * * *